(12) United States Patent
Hwang et al.

(10) Patent No.: US 6,869,621 B2
(45) Date of Patent: Mar. 22, 2005

(54) DIET COMPOSITION COMPRISING RAW FOODS AND DIETARY FIBERS

(75) Inventors: Sang Ho Hwang, Seoul (KR); Hey Eun Chang, Seoul (KR); Chang Won Choi, Kwacheo-shi (KR); Sung Bum Yang, Suwon-shi (KR); Mi Hyoun Park, Seoul (KR)

(73) Assignee: Eromlife Co., Ltd., Seoul (KR)

( * ) Notice: Subject to any disclaimer, the term of this patent is extended or adjusted under 35 U.S.C. 154(b) by 0 days.

(21) Appl. No.: 10/413,148

(22) Filed: Apr. 15, 2003

(65) Prior Publication Data

US 2004/0043056 A1 Mar. 4, 2004

(30) Foreign Application Priority Data

Nov. 8, 2002 (KR) ................................. 10-2002-0069128

(51) Int. Cl.[7] ................................................ A61K 35/78
(52) U.S. Cl. ................................................... 424/725
(58) Field of Search ................................. 424/725, 195.1

(56) References Cited

U.S. PATENT DOCUMENTS

| | | | |
|---|---|---|---|
| 5,484,593 A | 1/1996 | Iwasaki et al. | |
| 6,413,545 B1 | 7/2002 | Alviar et al. | |
| 6,472,002 B2 | 10/2002 | Liu et al. | |
| 2001/0002269 A1 * | 5/2001 | Zhao | .................... 426/112 |

FOREIGN PATENT DOCUMENTS

| | | |
|---|---|---|
| KR | 10-2001-0017229 | 3/2001 |
| KR | 10-2001-0103065 | 11/2001 |
| KR | 10-2002-0071325 | 9/2002 |

* cited by examiner

*Primary Examiner*—Patricia Leith
(74) *Attorney, Agent, or Firm*—Burns, Doane, Swecker & Mathis, L.L.P.

(57) ABSTRACT

The present invention relates to a diet composition comprising brown rice, job's tear, red beans, buckwheat, Italian millet, Indian millet, white beans, black beans, black rice, barley, brown rice sprouts, kale, matured pumpkin (Curcurbia moschata), carrot, Angelica, cabbage, wild Lanceolate root, Lotus root, radish, green radish, mugwort, pine needles, laver, sea mustard, sea tagle, Shiitake mushroom, Reishi mushroom, soy peptide, isolated soy protein, L-carnitine, Hibiscus extract, green tea extract and solomon's seal extract. The composition is useful in reducing body weight and body fat; controlling body shape; and lowering serum cholesterol and neutral fat.

3 Claims, 10 Drawing Sheets

DIET COMPOSITION COMPRISING RAW FOODS AND DIETARY FIBERS

This application claims priority under 35 U.S.C. §§119 and/or 365 to 10-2002-69128 filed in Korea on Nov. 8, 2002; the entire content of which is hereby incorporated by reference.

FIELD OF THE INVENTION

The present invention relates to a diet composition comprising raw foods and dietary fibers and more particularly, to a diet composition having an excellent effect on weight loss and the reduction of body fat and cholesterol as well as having enriched nutrition ingredients by comprising raw foods consisting of lyophilized powders of grains, vegetables and seaweeds; dietary fibers; and functional herbal extracts, etc.

BACKGROUND OF THE INVENTION

According to the development of industry and the growth of economy, nowadays our diet has been changing to a meat-based western style and accordingly, the ingestion amounts of vegetables and dietary fibers have been relatively reduced. Due to the collapse of such traditional diet, the ingestion of proteins, fats and calories has been increased and thus the physical standard of nation was improved. However, due to the over-ingestion of foods, the lack of physical exercise, stress, etc., physical strength was rather decreased and the amount of energy accumulated in body was increased, and thus obese patients show a tendency to rapidly increase. In fact, Health and Nutrition Examination Survey in Korea in 1992 showed that 19.4% of Korean males and 19.9% of Korean females were obese (Criteria: BMI 25) and especially, concerning the Korean housewives, the rate of obesity including over-weight was 24–36%.

Obesity refers to a condition where lots of fats are amassed in hypodermis in the body, and in general, it means a phenomenon where the remaining calories are excessively accumulated in the form of fat because the intake of energy exceeds its consumption amount. Obesity may become sufficiently problematic by itself and further, it may be a cause of adult diseases such as hypertension, diabetes, arteriosclerosis, stroke, angina pectoris and hyperlipidemia. That is, the obesity has become not only apparent problems but also major causes of giving rise to a big change in causes of human death and aspects of disease structure.

As the obesity becomes a current issue, lots of people have been greatly interested in diet methods to prevent and treat obesity. The purpose of diet to prevent or treat obesity should be the prevention or treatment of the complication of obesity as well as weight loss. In addition, the body weight cannot be re-gained after the treatment of obesity, thereby maintaining the optimum body weight that has been reduced. Recent studies recommend that obese persons reduce their weight by 5–10% of their initial weight rather than excessive weight loss to attain their standard weight, because even this can improve blood pressure, serum lipid, blood sugar, and insulin resistance, etc.

As the diet methods that have been hitherto known to prevent or treat the obesity, there are diet therapy, kinesiology, behavior modification therapy, etc., and in particular, the diet therapy can be the most fundamental and essential method for obese treatment. A desirable diet therapy should degrade the fats accumulated in body by reducing the calorie intake and increasing their consumption. As methods for restricting the calories, there are several methods according to their degree, but in general, a nutritionally-balanced 'low calorie diet (LCD)' is mostly utilized and operated principally through recipe using food exchange groups. However, in actually, one's dining behavior is very difficult to be modified and it is also extremely difficult for modern people to take a meal while considering food exchange groups.

Therefore, there is a need to develop foods capable of assisting obese people to operate nutritionally-balanced diet and at the same time, efficiently reducing their body fat. These days, a number of diet products have been on the market, but they have a difficulty of not being able to substitute meal. In addition, even in the case of substitute foods, there are lots of products having problems in nutrition balance. Moreover, in case of using diet supplements only, obese people may often neglect their meal management that should be improved fundamentally, and consequently they experience temporal diet success and repeated yo-yo phenomenon without doing right diet. That is, to improve people's health, it will be very important to develop substitute foods capable of supplying appropriate nutrition and calories, and of improving the meal habit of obese people and a health food effective in the reduction of body fat.

DETAILED DESCRIPTION OF THE INVENTION

The inventors found that in the course of studying foods capable of not only supplying appropriate calories by containing nutriments without omission but also effectively reducing body fat, a composition comprising lyophilized grains, vegetables, seaweeds and dietary fibers, and functional herbal extracts, etc. had effects of reducing body weight, body fat and other physical measurement values and that of decreasing the amounts of cholesterol and neutral fat, and thus have completed the present invention.

Therefore, it is an object of the present invention to provide a diet composition that is beneficial to health by comprising various nutrition ingredients without omission and is also capable of effectively improving obesity by losing body weight.

BRIEF DESCRIPTION OF THE DRAWINGS

1: In the Third Week 2: In the Sixth Week

1: In the Third Week 2: In the Sixth Week

1: In the Third Week 2: In the Sixth Week

1: In the Third Week 2; In the Sixth Week

1: In the Third Week 2: In the Sixth Week

1: In the Third Week 2: In the Sixth Week

1: In the Third Week 2: In the Sixth Week

1: Initial Total Cholesterol Amount
2: Total Cholesterol Amount in the Third Week
3: Total Cholesterol Amount in the Sixth Week

1: In the Third Week 2: In the Sixth Week

PREFERRED EMBODIMENT OF THE INVENTION

In order to achieve the object as mentioned above, the present invention provides a diet composition comprising 12–45% by weight of brown rice, 0.5–3% by weight of Job's tears, 0.5–3% by weight of red bean, 0.5–3% by weight of buckwheat, 0.5–2% by weight of Italian millet, 0.5–2% by weight of Indian mellet, 1–5% by weight of white bean, 0.5–3% by weight of black bean, 0.5–2% by weight of black rice, 1–5% by weight of barley, 6–20% by weight of sprout brown rice, 7–30% by weight of kale, 8–30% by weight of matured pumpkin (*Cucurbita moschata*), 0.5–3% by weight of carrot, 0.5–3% by weight of angelica, 0.5–3% by weight of cabbage, 0.01–1% by weight of wild lanceolate root, 0.1–1% by weight of burdock, 0.1–1% by weight of lotus root, 0.1–1% by weight of radish, 0.03–2% by weight of radish green, 0.001–1% by weight of mugwort, 0.001–1% by weight of pine needles, 0.001–1% by weight of laver, 0.001–1% by weight of sea mustard, 0.001–1% by weight of sea tangle, 0.001–1% by weight of shiitake mushroom, 0.001–1% by weight of reishi mushroom, 0.5–5% by weight of soy peptide, 0.5–5% by weight of isolated soy protein, 0.001–0.1% by weight of L-carnitine, 0.03–2% by weight of Hibiscus extract, 0.001–1% by weight of green tea extract and 0.001–1% by weight of Solomon's seal extract.

The present invention will be hereafter described in detail.

The diet composition according to the present invention is characterized in that it comprises grains, vegetables, seaweeds, mushrooms and herbs as main ingredients.

Particularly, the diet composition according to the present invention is characterized in that it comprises 12–45% by weight of brown rice, 0.5–3% by weight of Job's tears, 0.5–3% by weight of red bean, 0.5–3% by weight of buckwheat, 0.5–2% by weight of Italian millet, 0.5–2% by weight of Indian millet, 1–5% by weight of white bean, 0.5–3% by weight of black bean, 0.5–2% by weight of black rice, 1–5% by weight of barley, 6–20% by weight of sprout brown rice, 7–30% by weight of kale, 8–30% by weight of matured pumpkin (*Cucurbita moschata*), 0.5–3% by weight of carrot, 0.5–3% by weight of angelica, 0.5–3% by weight of cabbage, 0.01–1% by weight of wild lanceolate root, 0.1–1% by weight of burdock, 0.1–1% by weight of lotus root, 0.1–1% by weight of radish, 0.03–2% by weight of radish green, 0.001–1% by weight of mugwort, 0.001–1% by weight of pine needles, 0.001–1% by weight of laver, 0.001–1% by weight of sea mustard, 0.001–1% by weight of sea tangle, 0.001–1% by weight of shiitake mushroom, 0.001–1% by weight of reishi mushroom, 0.5–5% by weight of soy peptide, 0.5–5% by weight of isolated soy protein, 0.001–0.1% by weight of L-carnitine, 0.03–2% by weight of Hibiscus extract, 0.001–1% by weight of green tea extract and 0.001–1% by weight of Solomon's seal extract.

The brown rice is the grain abundant in nutrition ingredients such as dietary fibers effective in the prevention of constipation, vitamin B1 effective in the recovery of fatigue, vitamin E effective in the prevention of cancer, etc. It is preferred that the composition of the present invention comprises the brown rice as a source of carbohydrate. The composition according to the invention comprises preferably 12–45% by weight of the brown rice. Because the brown rice is a main source of carbohydrate, it is desirable for the composition of the invention to comprise it in the amount of not less than 12% by weight, and it is also desirable to comprise it in the amount of not more than 45% by weight in consideration of taste and balanced harmony with other several ingredients.

The Job's tears is the grain that abundantly contains not only carbohydrate, protein and fat but also calcium, potassium, iron, vitamin B1 and B2 and various enzymes In particular, it has been known to eliminate water unnecessary for body and help the circulation of blood while purifying it. In addition, it has an appetite suppress, uretic effect and antibacterial effect. The composition according to the invention comprises preferably 0.5–3% by weight of the Job's tears in consideration of nutritional aspect and harmony with other ingredients.

The red-bean is the grain that has carbohydrate such as starch and protein as main ingredients and it is good for nephritis or beriberi because it is abundant in vitamin B1. The composition according to the invention comprises preferably 0.5–3% by weight of the red-bean in consideration of nutritional aspect and harmony with other ingredients.

The buckwheat is the grain abundant in protein and fat, and it has been known to dispel constipation and have an effect on arteriosclerosis and hypertension. In particular, it has been known to help the degradation of unnecessary body fat as it contains lipase, which is a fat degradation enzyme. The composition of the invention comprises preferably 0.5–3% by weight of the buckwheat, because if its content is less than 0.5% by weight, the degradation effect of the body fat is weak while if it exceeds 3% by weight, this causes cost-push.

The Italian millet is the grain containing carbohydrate, protein, fat, vitamin B group, calcium, iron, etc. as main ingredients. It has been known to have an effect on diabetes, frequent urination, postpartum recovery and children's growth promotion, etc. The composition of the invention comprises preferably 0.5–2% by weight of the Italian millet because if its content is less than 0.5% by weight, the efficacy is weak while if it exceeds 2% by weight, this causes cost-push.

The Indian millet is the grain containing carbohydrate, protein, fat, vitamin B group, mineral and fiber, etc. as main ingredients. It has been known to have an effect on cardiovascular system, the promotion of digestion and drug detoxification, etc. The composition of the invention comprises preferably 0.5–2% by weight of the Indian millet because if its content is less than 0.5% by weight, it does not have any nutritional meanings while if it exceeds 2% by weight, this causes cost-push.

The white bean is the grain abundant in linoleic acid and contains a little glucose. It has been known to prevent arteriosclerosis by eliminating cholesterol and to be effective in the prevention of diabetes. In addition, asparaginic acid, which is in large quantities contained in the white bean, has been known to have efficacy in a hangover by eliminating the metabolic oxide of alcohol having strong toxicity. The composition of the invention comprises preferably 1–5% by weight of the white bean because if its content is less than 1% by weight, it does not have any nutritional meanings while if it exceeds 5% by weight, this causes cost-push.

The black bean is the grain abundant in protein, lipid and vitamin B1 and B2. It has been known to eliminate several poisons and have an effect on the acceleration of kidney system metabolism. The composition of the invention comprises preferably 0.5–3% by weight of the black bean in consideration of nutritional aspect and harmony with other ingredients.

The black rice is the grain abundant in iron and calcium. It has been known to have an effect on constipation, anemia, hypertension, diabetes, cancer and beauty, etc. The composition of the invention comprises preferably 0.5–2% by weight of the black rice because if its content is less than 0.5% by weight, the efficacy is weak while if it exceeds 2% by weight, this causes cost-push.

The barley contains fiber, calcium, iron and vitamin B group, etc., and has thus been known to have efficacy in diarrhea, diabetes, skin, constipation and poor blood circulation, etc. The composition of the invention comprises preferably 1–5% by weight of the barley because if its content is less than 1% by weight, this is not desirable in nutritional or sensual aspect while if it exceeds 5% by weight, it is difficult to be well harmonized with other ingredients.

The sprout brown rice refers to the brown rice that is germinated, and during the process of germination, specific medicinal components, not existing before the germination, are newly formed or remarkably increased, thereby components such as vitamin and amino acids are increased. Accordingly, it provides efficacy in easy bowel movement, the acceleration of energy metabolism, obesity, blood circulation and the promotion of natural healing ability, etc. The composition of the invention comprises the sprout brown rice preferably in the amount of not less than 6% by weight so that such efficacy can be sufficiently utilized and also comprises it preferably in the amount of not more than 20% by weight in consideration of the harmony of taste with other ingredients.

The kale contains carbohydrate, protein, vitamins, calcium, iron and chlorophyll, etc. It has been known to have efficacy in cancer, arteriosclerosis, liver trouble, gastroenteric trouble, obesity, nephropathy and anemia, etc. The composition of the invention comprises preferably 7–30% by weight of the kale because if its content is less than 7% by weight, the efficacy is weak while if it exceeds 30% by weight, this causes cost-push.

The matured pumpkin (Cucurbita moschata) is the vegetable abundant in carbohydrate and vitamin and has low calories. It has an effect of subsiding the swelling and has thus been known to be effective in waterborne obesity. The composition of the invention comprises preferably 8–30% by weight of the matured pumpkin (Cucurbita moschatal) in consideration of nutritional aspect.

The carrot contains vitamin A and vitamin B1, B2, C, etc., being abundant in calcium, magnesium, iron, etc., and has thus been known to have hematopoiesis. Accordingly, the carrot provides efficacy in fatigue recovery, constipation, diarrhea, neurasthenia and anemia. It also has been known to be effective in improvement of weak constitution. The composition of the invention comprises preferably 0.5–3% by weight of the carrot because if its content is less than 0.5% by weight, the efficacy is weak while if it exceeds 3% by weight, this causes cost-push.

The angelica is abundant in vitamin B group and germanium, etc. It has been known to have efficacy in hypertension, anemia, diabetes, neuralgia, urination, and fatigue recovery. In addition, it has the function of suppressing the agglomeration of platelets, and thus it can prevent the formation of thrombus. Accordingly, the composition of the invention comprises the angelica preferably in the amount of not less than 0.5% by weight so that such efficacy can be sufficiently utilized and also comprises it preferably in the amount of not more than 3% by weight in consideration of the harmony of taste with other ingredients.

The cabbage is the vegetable that contains a quantity of sulfur and chlorine, and it strengthens gastroenteric mucosa and cures ulcer. Especially, it is effective in the treatment of duodenal ulcer. It also has been known to be good for the treatment of alveolar pyorrhea when it is used with the carrot. In addition, it purifies blood and increases the resistance of body and being efficient for freckles, an acne and other skin diseases. Accordingly, the composition of the invention comprises the cabbage preferably in the amount of not less than 0.5% by weight so that such efficacy can be sufficiently utilized and also comprises it preferably in the amount of not more than 3% by weight in consideration of the harmony of taste with other ingredients.

The wild lanceolate root is the vegetable that contains saponin as a main ingredient, having been widely used for edible and medicinal purpose. It has been known to have hematopoiesis, anti-fatigue effect, blood pressure reduction, inflammation treatment and detoxification, etc. The composition of the invention comprises the wild lanceolate root preferably in the amount of 0.01–1% by weight because if its content is less than 0.01% by weight, the efficacy is weak while if it exceeds 1% by weight, this causes cost-push.

The burdock contains inulin and a little palmitic acid. It has been known to have an effect on urination, perspiration and sore throat. Accordingly, the composition of the invention comprises the burdock preferably in the amount of not less than 0.1% by weight so that the efficacy can be sufficiently utilized and also comprises it preferably in the amount of not more than 1% by weight in consideration of the harmony of taste with other ingredients.

The lotus root is the vegetable abundant in asparaginic acid and vitamin B12, etc. It has been known to have an effect on bleeding disorder, anemia and gastric ulcer. Accordingly, the composition of the invention comprises the lotus root preferably in the amount of not less than 0.1% by weight so that the efficacy can be sufficiently utilized and also comprises it preferably in the amount of not more than 1% by weight in consideration of the harmony of taste with other ingredients.

The radish contains a large quantity of vitamin C and its root contains amylase. Thus, it has a role in accelerating digestion. The radish green, the general term for the leaf and stem of the radish, has uretic effect and detoxification. And, it cures a disease symptomized by thirst, jaundice and suppurative mastitis. Arylisocyanate, the pungent ingredient of the radish green, has been known to have an anti-tumor effect. The composition of the invention comprises the radish and the radish green preferably in the amount of 0.1–1% by weight and 0.03–2% by weight, respectively, in consideration of taste and harmony with other ingredients.

The mugwort is the vegetable abundant in vitamin A, K, C and cineol. It has been known to have an effect on removal of fever, alleviation of pain, detoxification, extermination of insects and blood pressure reduction, etc. Accordingly, the composition of the invention comprises the mugwort preferably in the amount of not less than 0.001% by weight so that such efficacy can be sufficiently utilized and also comprises it preferably in the amount of not more than 1% by weight in consideration of the harmony of taste with other ingredients.

The pine needles mostly contain vitamin A, K, C and iron, enzymes, etc. It has been known to have an effect on hypertension, hypotension, anemia, hematopoiesis, blood purification, tonic and cholesterol reduction. Accordingly, the composition of the invention comprises the pine needles preferably in the amount of not less than 0.001% by weight so that such efficacy can be sufficiently utilized and also comprises it preferably in the amount of not more than 1% by weight in consideration of the harmony of taste with other ingredients.

The laver is seaweed abundant in vitamin A, B1, B2, C, K and calcium, phosphorus, etc. It has been known to have an effect on gastric/duodenal ulcer, anorexia, liver trouble and hypertension, etc. Accordingly, the composition of the invention comprises the laver preferably in the amount of not less than 0.001% by weight so that such efficacy can be sufficiently utilized and also comprises it preferably in the amount of not more than 1% by weight in consideration of the harmony of taste with other ingredients.

The sea mustard contains protein, vitamin A, B1, B2, C, calcium, phosphorus and iron, etc. It has been known to have an effect on constipation, obesity, metabolic acceleration and hematopoiesis, etc. Accordingly, the composition of the invention comprises the sea mustard preferably in the amount of not less than 0.001% by weight so that such efficacy can be sufficiently utilized and also comprises it preferably in the amount of not more than 1% by weight in consideration of the harmony of taste with other ingredients.

The sea tangle is seaweed that opulently contains vitamins, potassium, calcium, iron and iodine, etc. It has been known to have an effect on hypertension, nephropathy, arteriosclerosis, diabetes, gastric ulcer, heart disease, constipation, rheumatism and pernicious anemia, etc. Accordingly, the composition of the invention comprises the sea tangle preferably in the amount of not less than 0.001% by weight so that such efficacy can be sufficiently utilized and also comprises it preferably in the amount of not more than 1% by weight in consideration of the harmony of taste with other ingredients.

The shiitake mushroom is the mushroom that opulently contains carbohydrate, protein, fat, vitamin, potassium, calcium, phosphorus and iron, etc. It has been known to have efficacy in cancer, hypertension, heart disease, diabetes, stroke and the strengthening of cranial nerve, etc. The composition of the invention comprises preferably 0.001–1% by weight of the shiitake mushroom because if its content is less than 0.001% by weight, the efficacy is weak while if it exceeds 1% by weight, it is difficult to be well harmonized with other ingredients due to the peculiar strong taste of the shiitake mushroom.

The reishi mushroom eliminates cholesterol and other waste products in blood, and purifies blood. In addition, it has been known to have efficacy in disease of digestion system, disease of respiratory system, allergic bronchitis, bronchial asthma and acute/chronic liver trouble. The composition of the invention comprises preferably 0.001–1% by weight of the reishi mushroom because if its content is less than 0.001% by weight, the efficacy is weak while if it exceeds 1% by weight, this causes cost-push.

The soy peptide is the peptide having functionality, which is prepared by applying protease to the soy. It has been known to degrade body fat by activating brown adipose cells. The composition of the invention comprises preferably 0.5–5% by weight of the soy peptide in consideration of the efficacy, nutritional aspect, and harmony with other ingredients.

The isolated soy protein refers to a product made of the protein portion isolated from soybean. In addition, it is a nutritionally perfect vegetable protein source because carbohydrate and fat are almost eliminated. The composition of the invention comprises preferably 0.5–5% by weight of the isolated soy protein in consideration of nutritional aspect and harmony with other ingredients.

The L-carnitine is the natural substance that exists in various body organs and it is essential for the normal nutrition and metabolism of body. The L-carnitine is produced partially in the body, but should be supplied from the outside of body because its amount is absolutely insufficient. The composition of the invention comprises the L-carnitine preferably in the amount of not less than 0.001% by weight so that such efficacy can be sufficiently utilized and also comprises it preferably in the amount of not more than 0.1% by weight in consideration of harmony with other ingredients.

The Hibiscus extract is the extract obtained from Malvaceae plant called Hibiscus, containing HCA (hydroxy citric acid). It has been known to reduce body fat by increasing basic metabolic rate and accelerating fat metabolism in body. Accordingly, the composition of the invention comprises the Hibiscus extract preferably in the amount of not less than 0.03% by weight so that such efficacy can be sufficiently utilized and also comprises it preferably in the amount of not more than 2% by weight in consideration of harmony with other ingredients.

The green tea extract has been known to reduce body fat by accelerating fat degradation. Accordingly, the composition of the invention comprises the green tea extract preferably in the amount of not less than 0.001% by weight so that such efficacy can be sufficiently utilized and also comprises it preferably in the amount of not more than 1% by weight in consideration of harmony with other ingredients.

The Solomon's seal extract has been known to help diet to be more readily performed because it has blood sugar regulation, stress mitigation and hunger reduction effects. Accordingly, the composition of the invention comprises the Solomon's seal extract preferably in the amount of not less than 0.001% by weight so that such efficacy can be sufficiently utilized and also comprises it preferably in the amount of not more than 1% by weight in consideration of harmony with other ingredients.

In the mean time, the diet composition according to the present invention may comprise only the raw foods containing the above-mentioned lyophilized grains, seaweeds, vegetables and herbs. It may also be prepared by further adding 10–15 parts by weight of dietary fiber mixture comprising Psyllium Husk, chicory fiber, Garsinia Cambogia, molokheiya (*Corchorius olitorius* L.), Betasanne, kola nut (cola vera) extract, citrusbioflavonoid, vitamin C, lactose, alpha-starch, uncrystallized cellulose, xylitol, citric acid and citrus powder.

Particularly, the invention is characterized in that it provides the diet composition further adding 10–15 parts by weight of the dietary fiber mixture comprising 25–60% by weight of Psyllium Husk, 3–15% by weight of chicory fiber, 2–10% by weight of Garsinia Cambogia, 2–10% by weight of molokheiya (*Corchorius olitorius* L.), 1–5% by weight of Betasanne, 1–5% by weight of kola nut (cola vera) extract, 1–5% by weight of citrusbioflavonoid, 0.2–1% by weight of vitamin C, 10–30% by weight of lactose, 5–30% by weight of alpha-starch, 2–10% by weight of uncrystallized cellulose, 2–10% by weight of xylitol, 0.1–1% by weight of citric acid and 1–10% by weight of citrus powder, to the total 100 parts by weight of the above-described diet composition.

Psyllium Husk and chicory fiber can supplement dietary fiber that is apt to be lacking in modern diet because they are abundant in dietary fiber. Especially, Psyllium Husk absorbs water exceeding 40-folds of its own weight and when added to water, it forms a gel by forming a mucous layer, and thus it gives filling of fullness when ingested. Also, these dietary fibers assist in eliminating accumulation of feces and waste products adhered to intestinal wall and they make intestinal flora healthful and thus improve the physical condition of intestine. In consideration of efficacious aspect and harmony with other ingredients, it is preferred that the dietary fiber mixture comprises 25–60% by weight of the Psyllium Husk and 3–15% by weight of the chicory fiber.

Garsinia Cambogia is a natural fruit that has been used traditionally in south Asia region, and HCA (Hydroxy Citric Acid) is extracted from its peel and applied to the subject composition. HCA, which is a substance similar to citric acid that is contained in orange and citrus, is highly stable because it is a natural food and it has been known to exhibit no toxicity and resistance and to have effect of symptoms such as insomnia, nerve anxiety and hypochondria. That is, Garsinia Cambogia has an advantage of suppressing appetite by blocking the synthesis of fat and increasing the synthesis of glycogen without suppressing appetite by affecting central nervous system or stimulating the secretion of hormones. In consideration of efficacious aspect and harmony with other ingredients, it is preferred that the dietary fiber mixture comprises 2–10% by weight of the Garsinia Cambogia.

Molokheiya (*Corchorius olitorius* L.) is an annual yellow-green vegetable belonging to Tiliaceae and it grows spontaneously along the coast of the Mediterranean in Egypt. In spite of being a vegetable, molokheiya is very abundant in calcium and also abundant in dietary fibers and betacarotene as well as vitamin B group, and thus it has been known to be very effective in the decrease of cholesterol and neutral fat in liver. In consideration of efficacious aspect and harmony with other ingredients, it is preferred that the dietary fiber mixture comprises 2–10% by weight of the molokheiya.

Betasanne is a complex of chito acid and betaine hydrochloride, and it has been known to effectively block the accumulation of ingested fat in body by virtue of fat degradation and adsorption excretion effects. In consideration of efficacious aspect and harmony with other ingredients, it is preferred that the dietary fiber mixture comprises 1–5% by weight of the Betasanne.

The kola nut (cola vera) is a fruit of tropical plant belonging to Sterculiaceae, and it has been known to be effective in the decrease of body fat because it has no toxication. In consideration of efficacious aspect and harmony with other ingredients, it is preferred that the dietary fiber mixture comprises 1–5% by weight of the kola nut extract.

The citrusbioflavonoid, which is a flavonoid extracted from citrus, contains rutin, hesperidin, quercetin, naringin, etc. And it has been known to have an anti-oxidation effect, to be effective in improving the permeability of capillary vessel and blood circulation, and to have anti-allergy and anti-inflammation effects. In consideration of efficacious aspect and harmony with other ingredients, it is preferred that the dietary fiber mixture comprises 1–5% by weight of the Citrusbioflavonoid.

The alpha-starch forms a lucid or white colloidal solution with a very high viscosity when added to water. Such alpha starch having an increased viscosity shows a swelling phenomenon by the action of water and temperature and becomes vulnerable to enzyme reaction, and as a result, it can be readily digested. The dietary fiber mixture comprises preferably 5–30% by weight of the alpha-starch, because if its content is less than 5% by weight, the efficacy is insignificant and if it exceeds 30% by weight, the viscosity of the composition excessively increases.

Besides, in consideration of taste and nutritional aspect, it is preferred that vitamin C, lactose, uncrystallized cellulose, xylitol, citric acid and citrus powder are added in the dietary fiber mixture in amounts of 0.2–1% by weight, 10–30% by weight, 2–10% by weight, 2–10% by weight, 0.1–1% by weight and 1–10% by weight, respectively.

In the meantime, 8–30 parts by weight of alpha brown rice, 0.2–3 parts by weight of brewers yeast, 0.05–0.3 parts by weight of lactic acid bacteria powder, 5–20 parts by weight of oligosaccharide, 0.05–3 parts by weight of Momordicae grosvenori extract powder, 0.2–1 parts by weight of edible kelp meal and 0.5–5 parts by weight of vitamins or minerals may be further added in the final diet composition as additional materials for softness, to the total 100 parts by weight of the composition.

The diet composition as described above can be manufactured in the forms of liquids, powders or granules, but it is the most desirable to be manufactured in the form of powders so as to facilitate its ingestion.

The subject invention will be hereafter described with reference to the examples in detail.

However, the following examples are provided only to illustrate the invention; the matter of the invention should not be construed to be limited thereto.

EXAMPLE 1

Preparation of Raw Food Mixture Comprising Lyophilized Grains, Vegetables, Seaweeds, Etc.

Each ingredient was lyophilized according to "A process for the preparation of lyophilized foods of grains using surface instant sterilization" described in Korean Patent Application No. 2001-02145, and the lyophilized powders were mixed to thereby prepare a raw food mixture. That is to say, all ingredients in the grains, vegetables, seaweeds, etc. shown in Table 1 below were washed with clean water repeatedly several times. And they were chopped and crushed to a regular size or rapidly frozen at deep freezer of −40° C. as they were after non-edible portions were sufficiently eliminated. The rapidly-frozen ingredients were dried in lyophilizer using the prior art according to their characteristics, and then each ingredient was smashed to the size capable of passing through a sieve of 60 meshes and mixed with the mixing ratios as shown in Table 1 to thereby prepare the raw food mixture.

TABLE 1

| Category | Ingredient | Mixing Ratio (wt. %) |
| --- | --- | --- |
| Grains | Brown Rice | 33.1 |
|  | Job's Tears | 1 |
|  | Red Bean | 1.2 |
|  | Buckwheat | 1.2 |
|  | Italian Millet | 0.6 |
|  | Indian Millet | 0.7 |
|  | White Bean | 3.3 |
|  | Black Bean | 1.3 |
|  | Black Rice | 0.6 |
|  | Barley | 2.4 |
|  | Sprout Brown Rice | 13.05 |
| Vegetables | Kale | 15.2 |
|  | Matured pumpkin (*Cucurbita moschata*) | 18.5 |
|  | Carrot | 0.6 |
|  | Angelica | 0.6 |
|  | Cabbage | 0.66 |
|  | Wild Lanceolate Root | 0.07 |
|  | Burdock | 0.35 |
|  | Lotus Root | 0.3 |
|  | Radish | 0.3 |
|  | Radish Green | 0.17 |
|  | Mugwort | 0.01 |
|  | Pine Needled | 0.01 |
| Seaweeds | Layer | 0.002 |
|  | Sea Mustard | 0.002 |
|  | Sea tangle | 0.002 |
| Mushrooms | Shiitake Mushroom | 0.02 |
|  | Reishi Mushroom | 0.02 |
| Functional Groups | Soy Peptide | 2.4 |
|  | Isolated Soy Protein | 2.09 |
|  | L-carnitine | 0.02 |
|  | Hibiscus Extract | 0.2 |
|  | Green Tea Extract | 0.01 |
|  | Solomon's Seal Extract | 0.014 |
| Total |  | 100 |

EXAMPLE 2

Preparation of Diet Composition Comprising Lyophilized Grains, Vegetables, Seaweeds, etc., Dietary Fibers and Functional Extracts The ingredients of the dietary fibers and functional extracts shown in Table 2 below were mixed with the given mixing ratio to thereby prepare a dietary fiber mixture. Thereafter, 13.75 parts by weight of the dietary fiber mixture was added to 100 parts by weight of the raw food mixture prepared in Example 1 to prepare a diet composition.

TABLE 2

| Ingredient | Mixing Ratio (wt. %) |
| --- | --- |
| Psyllium Husk | 45 |
| Chicory Fiber | 5 |
| Garsinia Cambogia | 4 |
| Molokheiya | 2.5 |
| Betasanne | 2 |
| Kola Nut Extract | 2 |

TABLE 2-continued

| Ingredient | Mixing Ratio (wt. %) |
| --- | --- |
| Citrusbioflavonoid | 2 |
| Vitamin C | 0.5 |
| Lactose | 15 |
| Alpha-Starch | 8 |
| Uncrystallized Cellulose | 4.5 |
| Xylitol | 6 |
| Citric Acid | 0.4 |
| Citrus powder | 3.1 |
| Total | 100 |

Experiment 1

Clinical Test

The clinical test to investigate whether or not the compositions according to the invention are effective in the improvement of obesity was applied to 54 healthy females of 25–35 ages whose body mass index is not less than 25 and it was conducted according to blind method. Weights and heights of all subjects were measured, and physical measurements, body components, metabolic variables, abdominal ultrasound and general internal tests were performed under the empty stomach condition of at least 8 hours or longer in the initial visit, the third week and the sixth week. They were requested to record their diet diary steadily and turn it in.

The subjects were divided into three groups by 18 persons at random. That is, the experiment was carried out in divided three groups; A group where the subjects ingested the composition of the lyophilized raw food mixture adding the dietary fibers and functional extracts, prepared in Example 2, B group where the subjects ingested only the lyophilized raw food mixture prepared in Example 1, and control group where the subjects were allowed to take a normal meal but instead, they were given continuous nutrition education by a professional dietitian. There were no statistical differences in their initial body weight, statistical population variables and body shape.

The average age of the subjects was 29.99±0.43 (mean±SD) and average initial body fat rate was 35.18±4.15%. The average body weight was 71.89±10.40 kg, initial waist was 84.58±9.55 cm, and initial hip was 100.27±5.84 cm.

Figure 1:
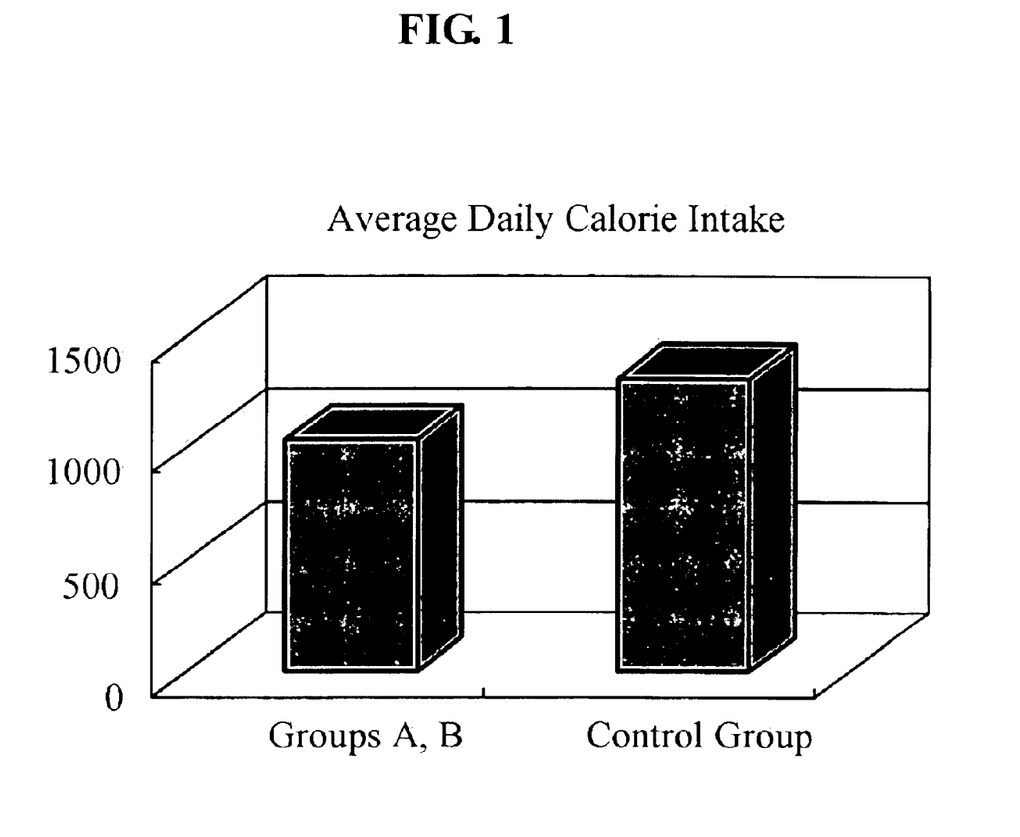
FIG. 1 is a graph showing average daily calorie intake in experimental groups that ingested the composition of the invention and in control group that was given only nutrition education.

1-1) Comparison Analysis of the Daily Calorie Intake According to Ingestion of the Diet Composition The test subjects were subjected to ingest the raw food mixture prepared in Example 1 and the composition prepared in Example 2 and to turn in their diet diary in which all foods ingested during the test period were recorded. The diet diary was analyzed using CAN-Pro to determine calories and nutriment intake. As a result, as shown in FIG. 1, average daily calorie intake in experimental groups A and B was 1042.61±179.73 kcal on the average, and the control group showed 1313.49±308.07 kcal. That is, it was revealed that the groups, which ingested the compositions prepared in the invention, ingested less calorie than the control group, and thus it can be concluded that the compositions of the invention provides young corpulent women with an effective way of reducing calorie intake during a short period.

Figure 2:
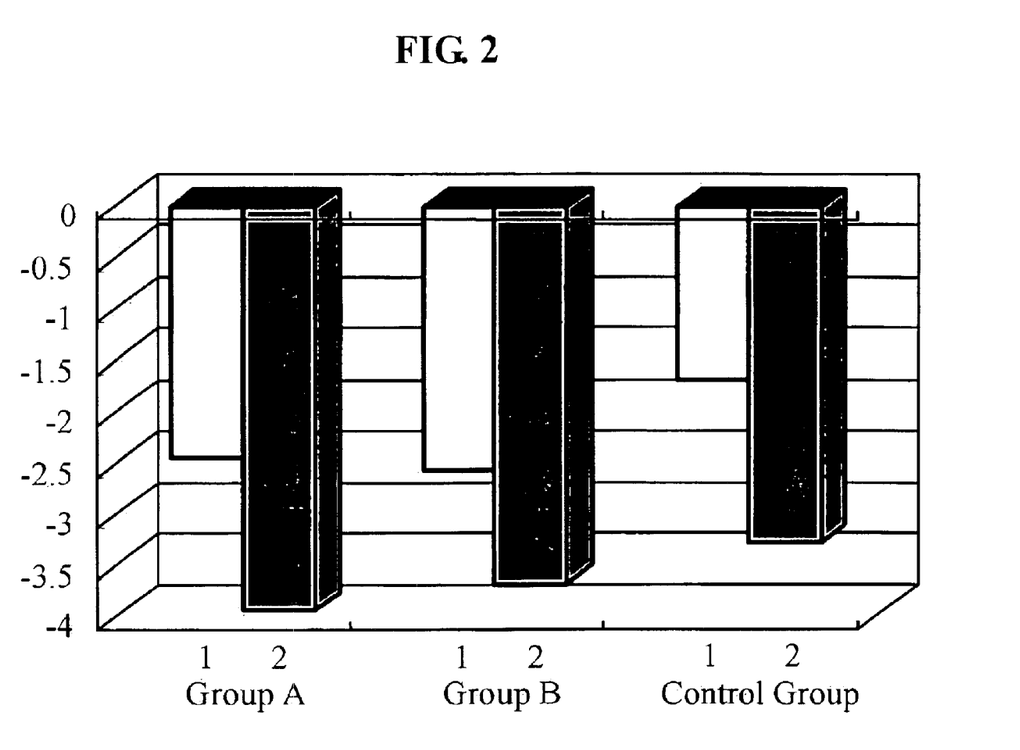
FIG. 2 is a graph showing changes in the weight in experimental groups that ingested the composition of the invention and in control group that was given only nutrition education.

1-2) Comparison of Body Weight and Body Components According to Ingestion of the Diet Composition After the test subjects ingested the raw food mixture prepared in Example 1 and the composition prepared in Example 2, their body weight was each measured. As a result, as shown in FIG. 2, in the sixth week, which is the termination period of the test, the subjects exhibited body weight loss in the order of A, B, and control group. That is, A group, B group and the control group showed the change of −3.94±2.23 kg, −3.69±1.67 kg, and −3.29±2.25 kg on the average, respectively, and thus it can be seen that the weight can be reduced by ingesting the composition of the invention.

Figure 3:
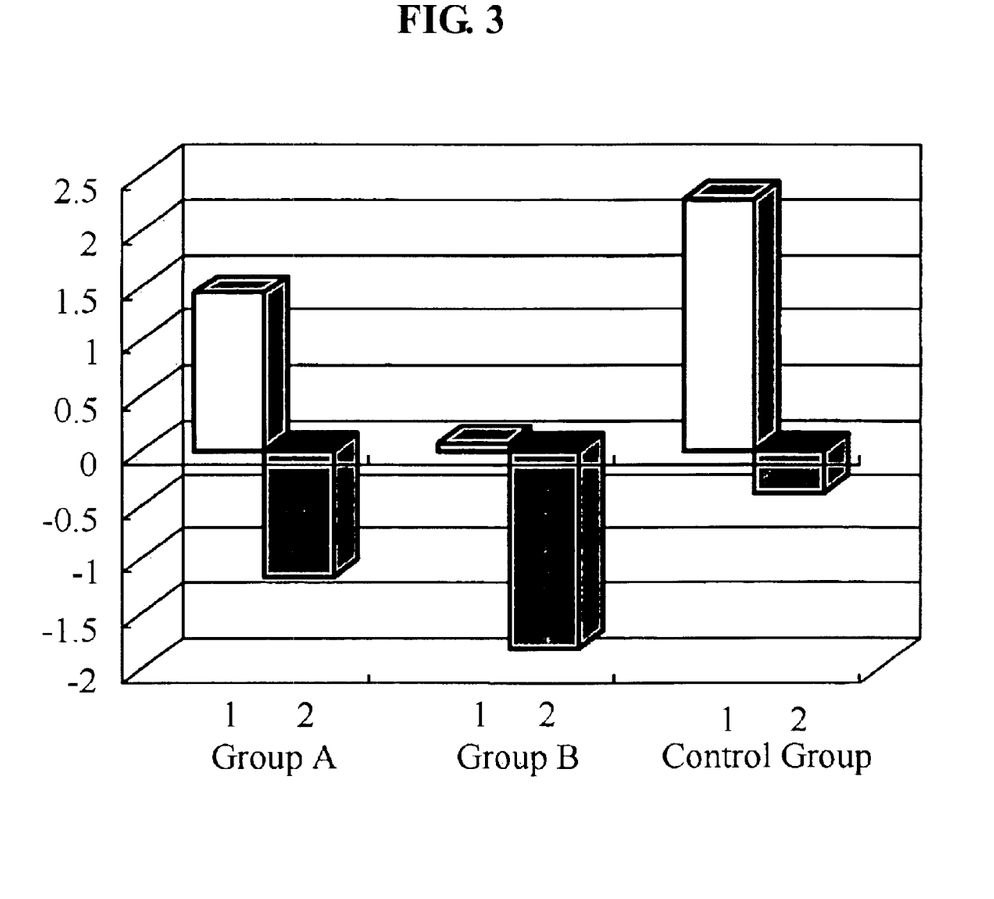
FIG. 3 is a graph showing changes in the body fat in experimental groups that ingested the composition of the invention and in control group that was given only nutrition education.

Also, the body fat of each test subject was measured using Bioimpedance Analyser (Vanilla, USA). And as a result, as shown in FIG. 3, in all three groups, body fat was transiently increased in the third week. But in the sixth week, which is the termination period of the test, the body fat was decreased in the order of B, A, and control group. Accordingly, it can be seen that the body fat can be reduced by ingesting the composition of the invention.

Figure 4:
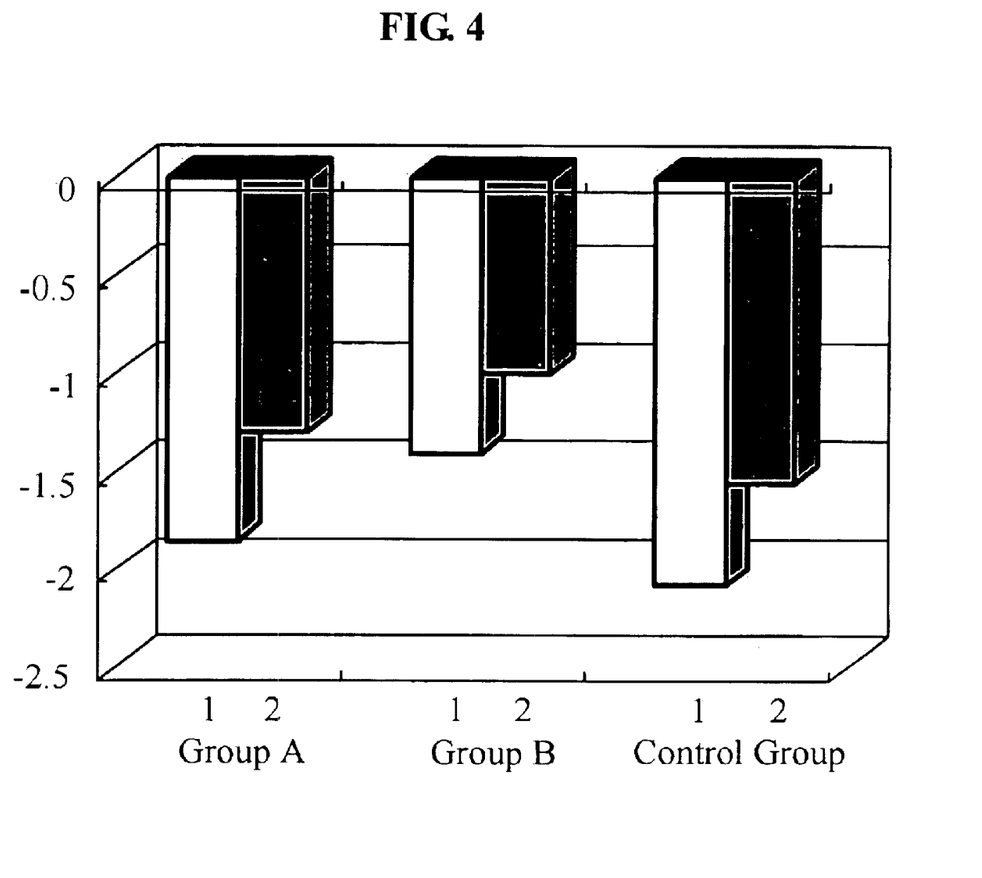
FIG. 4 is a graph showing changes in the body water in experimental groups that ingested the composition of the invention and in control group that was given only nutrition education.

Also, the body water of each test subject was measured using Bioimpedance Analyser. And as a result, as shown in FIG. 4, in A and B groups, the body water (reduction) amount was less than that of the control group. And in the sixth week, which is the termination period of the test, the body water amount was reduced in the order of the control group, A group and B group.

When putting together the above results, we can conclude that the compositions of the invention can become a food effective in improving obesity.

1-3) Comparison of Body Shape According to Ingestion of the Diet Composition

After the test subjects ingested the raw food mixture prepared in Example 1 and the composition prepared in Example 2, the diet effects of the compositions prepared in the invention were investigated by measuring the waist, hip and girth of thigh.

Figure 5:
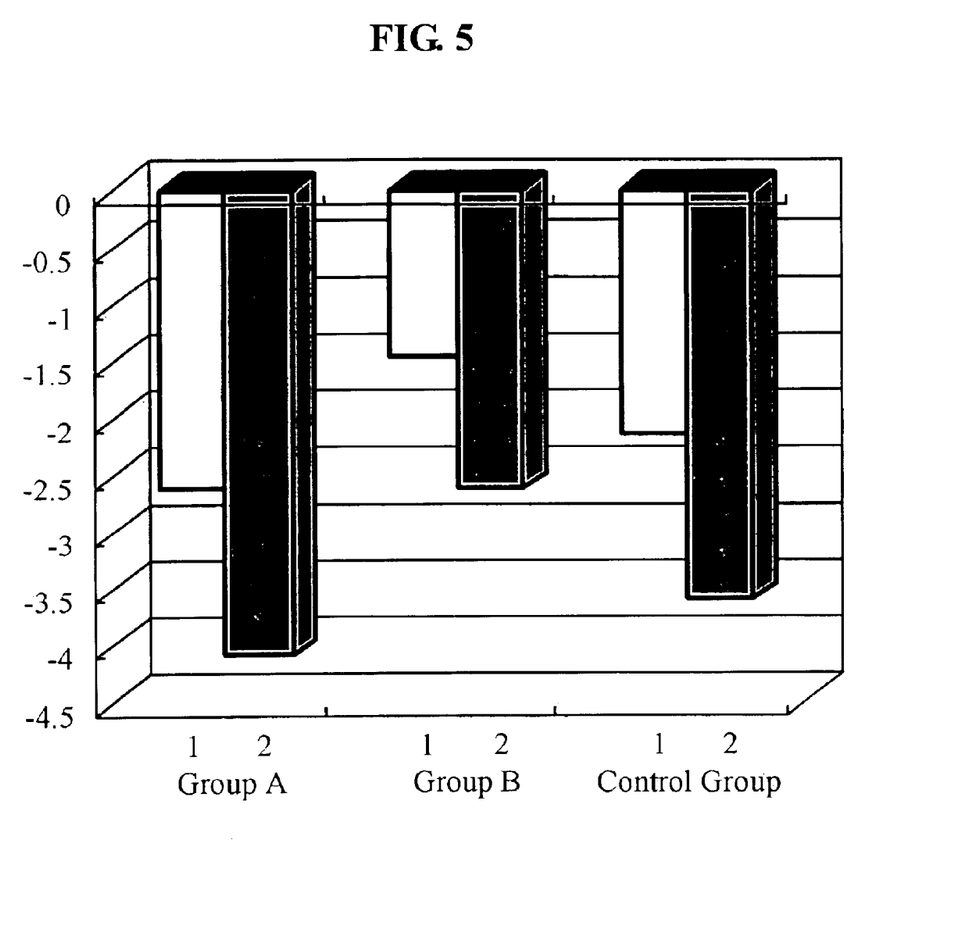
FIG. 5 is a graph showing changes in the waist in experimental groups that ingested the composition of the invention and in control group that was given only nutrition education.

First, as a result of the measurement of a change in the waist, as shown in FIG. 5, the waist was reduced in the order of A group, the control group and B group.

Figure 6:
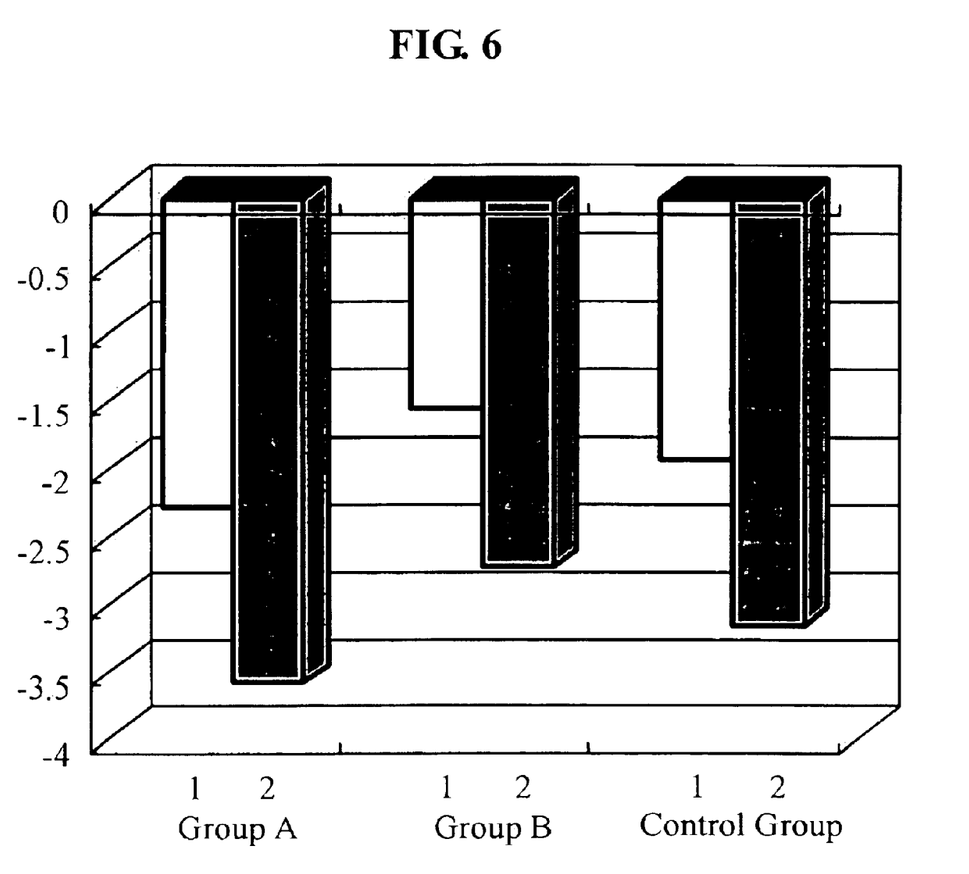
FIG. 6 is a graph showing changes in the hip in experimental groups that ingested the composition of the invention and in control group that was given only nutrition education.

Also, as a result of the measurement of a change in the hip, as shown in FIG. 6, the hip was reduced in the order of A group, the control group and B group.

Figure 7:
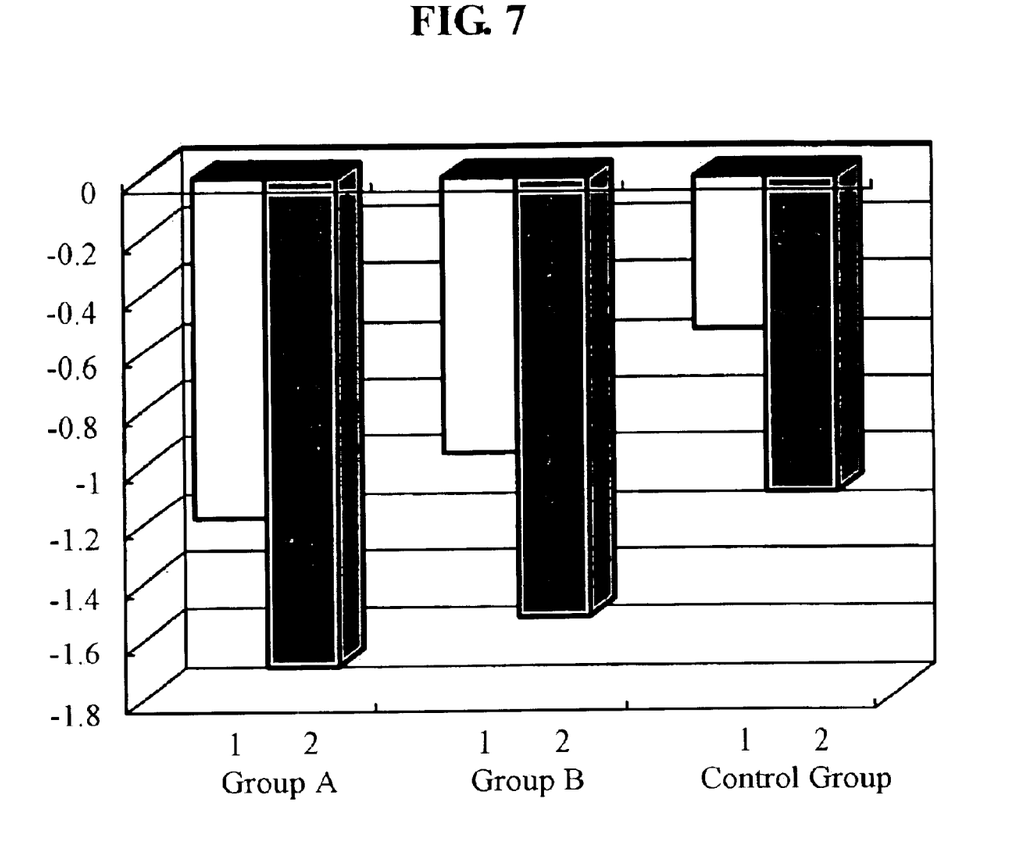
FIG. 7 is a graph showing changes in the girth of right thigh in experimental groups that ingested the composition of the invention and in control group that was given only nutrition education.
Figure 8:
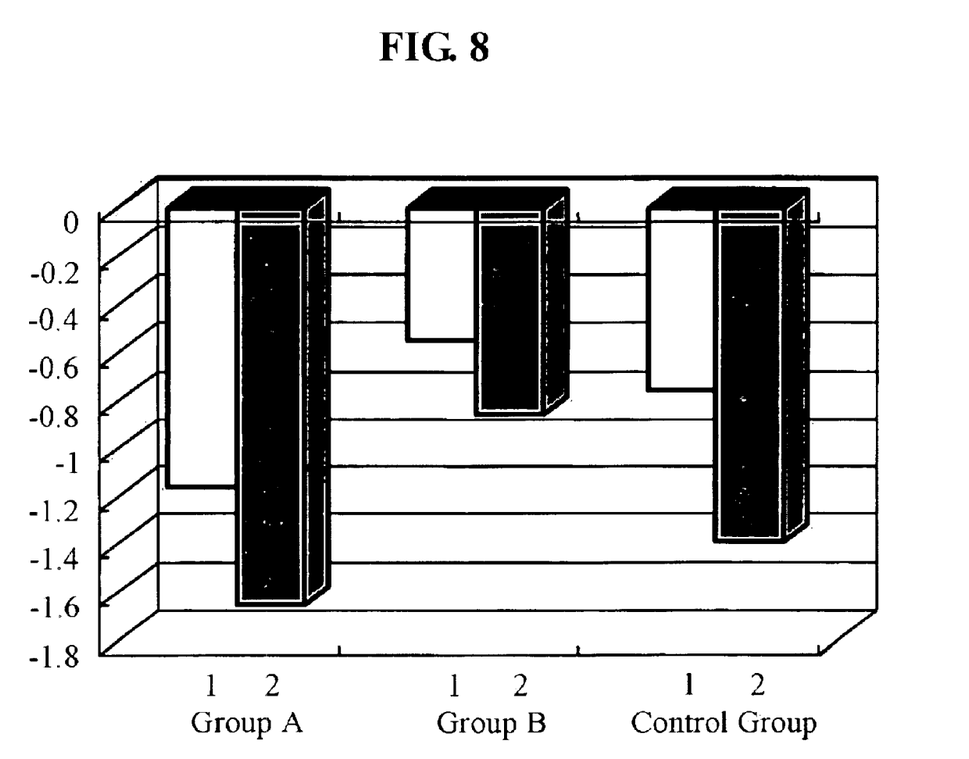
FIG. 8 is a graph showing changes in the girth of left thigh in experimental groups that ingested the composition of the invention and in control group that was given only nutrition education.

As a result of the measurement of a change in the girth of left/right thigh, as shown in FIG. 7 and FIG. 8, it was observed that the girth of thigh was reduced by about 1.2–1.7 cm in all groups. And in the case of girth of right thigh (see FIG. 7), it was reduced in the order of A group, B group, and the control group whereas in the case of girth of left thigh (see FIG. 8), it was reduced in the order of A group, the control group, and B group.

Consequently, it can be seen that the physical dimension can be reduced by ingesting the composition of the invention and thereby the obesity can be effectively improved.

Figure 9:
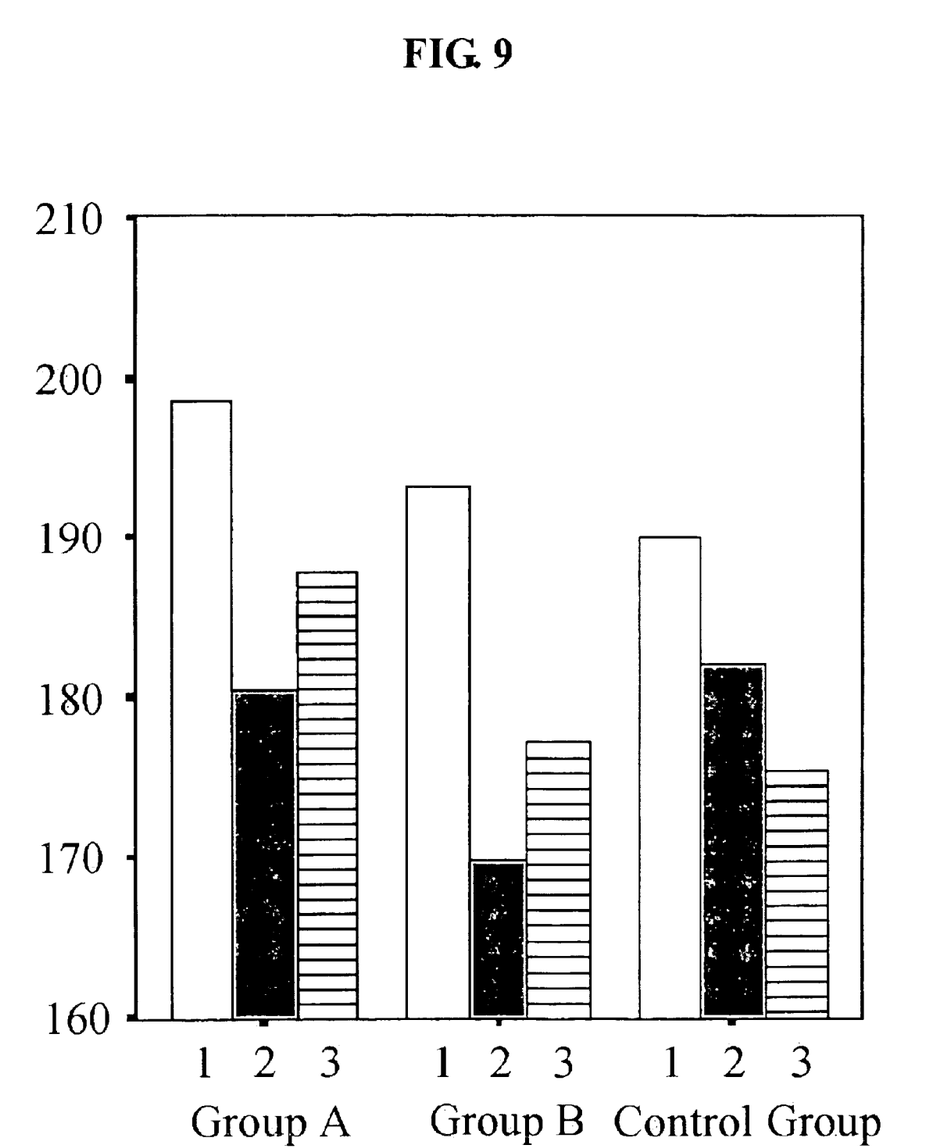
FIG. 9 is a graph showing changes in the total blood cholesterol amount in experimental groups that ingested the composition of the invention and in control group that was given only nutrition education.

1-4) Comparison of Fat Metabolism Related Item According to Ingestion of the Diet Composition After the test subjects ingested the mixture prepared in Example 1 and the composition prepared in Example 2, respectively, their total cholesterol amount in blood was determined using HITACHI 7600 (Hitachi, Japan). In the determination of the cholesterol amount, T-CHO (T-cholesterol, Randox, UK) was used as a reagent. As a result, as shown in FIG. 9, the amount was decreased in all of A group, B group and the control group and especially, B group and the control group exhibited a statistically significant decrease.

Figure 10:
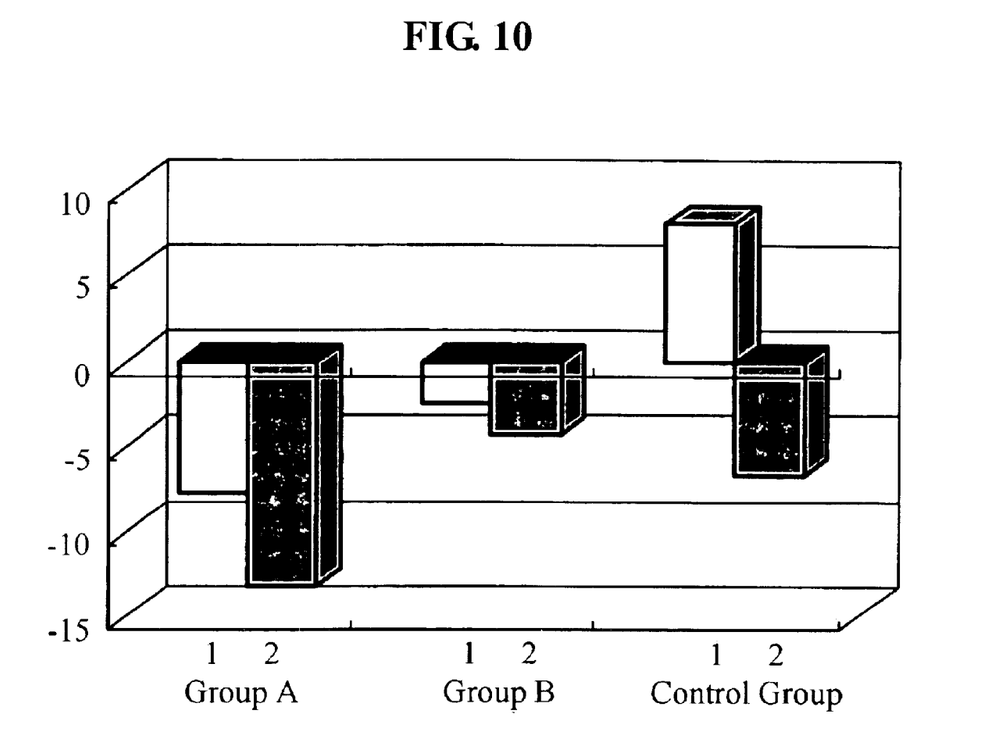
FIG. 10 is a graph showing changes in the blood neutral fat amount in experimental groups that ingested the composition of the invention and in control group that was given only nutrition education.

Also, the neutral fat amount in blood in each test subject was determined using HITACHI 7600. In the determination of the neutral fat amount, TG (triglyceride, Randox, UK) was used as a reagent. As a result, as shown in FIG. 10, in A and B groups, the amount was gradually decreased in both third week and sixth week, whereas in the control group, the amount was transiently increased in the third week and was decreased again. Also, A group showed the most decreased amount of the neutral fat. Consequently, it can be seen that the fat amount can be decreased by ingesting the composition of the invention, and thereby the obesity can be improved.

In addition, the albumin level in blood in each test subject was determined by chromometry using HITACHI 7600 (Hitachi 7600-110, Hitachi, Japan). And as a result, as shown in Table 3 below, it can be seen that the level was within the normal range. The reagent used to determine the albumin level was ALB (Sinyang, Korea).

Further, the AST (Aspartate Transaminase) and ALT (Alanine Transaminase) levels in each test subject were determined by UV method using HITACHI 7600. And as a result, as shown in Table 3 below, it can be seen that all levels were within the normal ranges. The reagents used to determine the AST and ALT were AST (Sinyang, Korea) and ALT (Sinyang, Korea), respectively.

Furthermore, the blood of each test subject was determined using ADVIA 120 (Automated Hematology analyser). And as a result, all levels of hemoglobins, platelets and white blood cells were within the normal ranges. This means that the compositions of the invention have efficacy in body weight loss and body fat degradation by effectively acting on fat metabolism and at the same time, they are stable in respect of liver cell level and nutriment metabolism, blood composition and so on.

TABLE 3

| Test Item | Experimental Groups | Initial | Third Week | Sixth Week | Normal Range |
|---|---|---|---|---|---|
| Albumin (mg/dL) | A Group | 4.59_0.30 | 4.59_0.18 | 4.41_0.25 | 3.5–5.3 |
| | B Group | 4.53_0.15 | 4.54_0.24 | 4.64_0.21 | |
| | Control Group | 4.77_0.46 | 4.58_0.27 | 4.51_0.23 | |
| AST (unit/L) | A Group | 20.90_7.71 | 21.80_8.46 | 19.00_4.35 | 8–40 |
| | B Group | 28.00_15.50 | 27.29_11.51 | 21.71_4.64 | |
| | Control Group | 26.67_23.32 | 20.13_8.32 | 20.44_4.80 | |
| ALT (unit/L) | A Group | 12.40_3.44 | 14.00_5.23 | 13.10_5.92 | 6–35 |
| | B Group | 27.57_24.51 | 24.86_15.71 | 18.00_9.45 | |
| | Control Group | 14.67_6.93 | 13.88_4.19 | 14.89_7.62 | |

TABLE 3-continued

| Test Item | Experimental Groups | Initial | Third Week | Sixth Week | Normal Range |
|---|---|---|---|---|---|
| Hemoglobin (mg/dL) | A Group | 12.63_0.81 | 12.38_1.42 | 12.29_0.96 | 12–16 |
| | B Group | 12.66_0.84 | 12.64_1.83 | 12.94_1.24 | |
| | Control Group | 12.59_0.55 | 12.36_0.86 | 12.27_0.42 | |
| Platelet (mg/dL) | A Group | 250.60_68.02 | 267.70_66.87 | 253.90_69.42 | 140–440 |
| | B Group | 249.29_49.96 | 269.43_71.54 | 247.71_45.39 | |
| | Control Group | 241.11_73.37 | 267.25_44.60 | 250.89_37.80 | |
| WBC (mg/dL) | A Group | 5.94_1.06 | 5.49_1.29 | 6.12_1.47 | 4.0–10.0 |
| | B Group | 6.61_1.57 | 6.27_2.03 | 6.63_1.84 | |
| | Control Group | 6.23_1.28 | 6.10_1.64 | 6.41_1.38 | |

Industrial Applicability

The composition according to the present invention is effective in reduction of weight and body fat and body shape management as well as abundant in nutrition ingredients. And also the composition has an excellent effect on decreasing cholesterol and neutral fat amounts. Therefore, the composition according to the invention can be usefully employed as a food capable of preventing or improving obesity while assisting in ingesting nutriments, which are apt to be lacking in modern people, without omission.

What is claimed is:

1. A diet composition comprising 12–45% by weight of brown rice, 0.5–3% by weight of Job's tear, 0.5–3% by weight of red bean, 0.5–3% by weight of buckwheat, 0.5–2% by weight of Italian millet, 0.5–2% by weight of Indian millet, 1–5% by weight of white bean, 0.5–3% by weight of black bean, 0.5–2% by weight of black rice, 1–5% by weight of barley, 6–20% by weight of brown rice sprouts, 7–30% by weight of kale, 8–3% by weight of matured pumpkin (Cucurbita moschata), 0.5–3% by weight of carrot, 0.5–3% by weight of Angelica, 0.5–3% by weight of cabbage, 0.01–1% by weight of wild Lanceolate root, 0.1–1% by weight of burdock, 0.1–1% by weight of lotus root, 0.1–1% by weight of radish, 0.03–2% by weight of green radish, 0.001–1% by weight of mugwort, 0.001–1% by weight of pine needles, 0.001–1% by weight of laver, 0.001–1% by weight of sea mustard, 0.001–1% by weight of sea tangle, 0.001–1% by weight of Shiitake mushroom, 0.001–1% by weight of Reishi mushroom, 0.5–5% by weight of soy peptide, 0.5–5% by weight of isolated soy protein, 0.001–0.1% by weight of L-carnitine, 0.03–2% by weight of Hibiscus extract, 0.001–1% by weight of green tea extract and 0.001–1% by weight of Solomon's seal extract.

2. The diet composition of claim 1, wherein the composition further comprises 10–15 parts by weight of dietary fiber mixture consisting of 25–60% by weight of Psyllium Husk, 3–15% by weight of Chicory fiber, 2–10% by weight of Garsinia Cambogia, 2–10% by weight of molokheiya (*Corchorius olitorius* L.), 1–5% by weight of Betasanne, 1–5% by weight of kola nut (cola vera) extract, 1–5% by weight of citrus bioflavonoid, 0.2–1% by weight of vitamin C, 10–30% by weight of lactose, 5–30% by weight of alpha-starch, 2–10% by weight of uncrystallized cellulose, 2–10% by weight of xylitol, 0.1–1% by weight of citric acid and 1–10% by weight of citrus powder, to the total 100 parts by weight of said composition.

3. The diet composition of claim 1, wherein the diet composition further comprises 8–30 parts by weight of alpha brown rice, 0.2–3 parts by weight of brewers yeast, 0.05–0.3 parts by weight of lactic acid bacteria powder, 5–20 parts by weight of oligosaccharide, 0.05–3 parts by weight of Momordicae grosvenori extract powder, 0.2–1 parts by weight of edible kelp meal and 0.5–5 parts by weight of vitamins or minerals, to the total 100 parts by weight of said composition.

* * * * *